United States Patent [19]

Winters

[11] 3,974,308

[45] Aug. 10, 1976

[54] METHOD FOR TREATING A DISPOSABLE SURGICAL DRAPE

[75] Inventor: Terry L. Winters, Neenah, Wis.

[73] Assignee: Kimberly-Clark Corporation, Neenah, Wis.

[22] Filed: June 10, 1975

[21] Appl. No.: 585,763

Related U.S. Application Data

[60] Division of Ser. No. 458,315, April 5, 1974, Pat. No. 3,902,484, which is a continuation of Ser. No. 223,090, Feb. 7, 1972, abandoned.

[52] U.S. Cl. .............................. 427/244; 427/256; 428/311; 428/425; 428/474; 252/8.8
[51] Int. Cl.² ........................ B05D 5/12; B32B 5/18
[58] Field of Search ...................... 427/244; 252/8.8; 128/132 D; 260/2.5 AD, 2.5 AG; 428/311, 425

[56] References Cited

UNITED STATES PATENTS

| | | | |
|---|---|---|---|
| 3,124,536 | 3/1964 | Ware | 252/8.8 X |
| 3,190,763 | 6/1965 | Schleede et al. | 128/132 D |
| 3,249,465 | 5/1966 | Chen | 260/2.5 AD |
| 3,668,050 | 6/1972 | Donnelly | 128/132 D |
| 3,738,359 | 6/1973 | Lindquist et al. | 128/132 D |
| 3,826,674 | 7/1974 | Schwarz | 428/311 |

FOREIGN PATENTS OR APPLICATIONS

| | | | |
|---|---|---|---|
| 664,595 | 6/1963 | Canada | 252/8.8 |
| 665,732 | 6/1963 | Canada | 260/2.5 AD |

*Primary Examiner*—Michael R. Lusignan
*Assistant Examiner*—Evan K. Lawrence
*Attorney, Agent, or Firm*—Leydig, Voit, Osann, Mayer & Holt, Ltd.

[57] ABSTRACT

A normally hydrophobic, open-celled polyurethane foam for use on the surface of a disposable surgical drape is treated with the reaction product of a mineral acid and a fatty acid tertiary amine, wherein the amine is partially neutralized to a fatty acid tertiary ammonium salt which renders the foam material antistatic, while providing increased rates of fluid absorption and reduced tendency for lathering when the foam material is rubbed with water present on the foam material. An improved disposable surgical drape comprises an outer layer of the treated foam bonded to a fluid-impervious plastic layer attached to a fibrous base sheet.

5 Claims, 2 Drawing Figures

METHOD FOR TREATING A DISPOSABLE SURGICAL DRAPE

This is a division of application Ser. No. 458,315 filed Apr. 5, 1974, now U.S. Pat. No. 3,902,484, Ser. No. 458,315 being a continuation of Ser. No. 223,090 filed Feb. 7, 1972 and now abandoned.

RELATED APPLICATIONS

Donnelly, Ser. No. 17,431, filed Mar. 9, 1970, now U.S. Pat. No. 3,668,050. Schrading and Winters, Ser. No. 58,336, filed July 27, 1970, now U.S. Pat. No. 3,669,106.

DESCRIPTION OF THE INVENTION

The present invention relates generally to disposable surgical drapes and, more particularly to surgical drapes having an absorbent foam material covering the primary operative area.

There have been many new commercial developments in disposable articles for use in hospitals, clinics, and the like, particularly with respect to surgical drapes that are intended for only a single use. Since such disposable surgical drapes are less expensive to initially produce, coupled with the fact that they need not be laundered and sterilized for repeated uses, this has resulted in their capturing a significant commercial market, which is generally predicted to increase as labor costs associated with laundering and other handling increase. Among the more significant recent developments in disposable surgical drapes are those drapes disclosed in the Donnelly application Ser. No. 17,431, filed Mar. 9, 1970, now U.S. Pat. No. 3,668,050; as well as the Scrading and Winters application, Ser. No. 58,336, filed July 27, 1970, now U.S. Pat. No. 3,669,106; all of which are assigned to the assignee of the present invention.

Features common to the surgical drape disclosed in these applications involve a fibrous base sheet and a sheet of fluid impervious plastic film attached to the base sheet as well as a fluid absorbent plastic foam material bonded to the plastic film in the primary operative area of the surgical drape.

Preliminary to a detailed description of the improved surgical drape of the present invention, it should be pointed out that the use of open-celled foam material in at least the primary operative area, including the fenestration area of a laparotomy sheet, for example, has experienced widespread acceptance, particularly when it is combined with an underlayer of fluid impervious plastic or film, since the combination is strong and abrasion resistant even when exposed to liquids and when subjected to the physical contact and manipulation that are encountered during the course of an operation. A laparotomy sheet is an elongated generally rectangular sheet used to cover the patient during thoracic or abdominal surgery, and is typically about 6 to 8 feet in length and about 3 to 6 feet in width. The layer or film of fluid impervious plastic prevents the liquid encountered during operating procedures from striking through the sheet and thereby prevents passage of bacteria through the sheet. Moreover, the foam material has a high frictional coefficient that prevents dislodgement of surgical instruments, supplies and the like when placed on the surface of the sheet during an operation. The foam material is stable at conditions encountered during sterilization treatments either by steam of ethylene oxide or the like, and the combination of film and foam material has good draping characteristics which are desirable for conforming the drape to the patient during an operation. The open-celled foam material is also fluid absorbent to minimize fluid run-off that is invariably encountered during most operations.

When drapes are used in anesthetizing locations, it is of utmost importance to prevent sparking due to the buildup of static electrical charges on the drapes, which can be hazardous since explosive anesthetizing gases and oxygen are often present in operating rooms. The governing criteria for electrical surface resistivity of fabrics used in anesthetizing locations is set forth in the Code for the Use of Flammable Anesthetics (1960), published by the National Fire Protection Association in their publication No. 56 (hereinafter referred to as the Code). Appendix A, Section 3513-Textiles, requires that the surface resistivity of the fabric should be measured at an ambient humidity of 50% and a temperature of 23°C by method 76–59 of the American Association of Textile Chemists and Colorists (U.S.A.C.L. 14.112–1961) and states that the measured value should be less than $5 \times 10^{11}$ ohms per square unit of the material.

Although many chemical treatments are known to provide antistatic properties when applied to hydrophobic fibers, films and other surfaces, many of such treatments have been found to be deficient in one or more respects. For example, some compounds are simply unsuitable in that they fail to provide sufficient conductivity or, in other words, fail to lower the surface resistivity to acceptable limits or values that satisfy the hereinbefore identified standard when applied to materials used in locations that have flammable anesthetics. Other chemicals are soluble only with isopropanol, which is flammable and thus creates a hazardous environment and may require expensive explosion-proof processing equipment for its use. Additionally, other antistatic agents, when applied to foam materials, exhibit a severe lathering characteristic when treated material is rubbed with water present on the material. Still other chemical treatments are unsuitable because their use during the process of treating the material is accompanied by the presence of irritating vapors. Similarly, with some chemicals the resulting treated material may cause dermatological problems with patients or others coming in contact therewith.

One chemical that is available as an antistatic agent is a fatty acid tertiary amine having the structural formula:

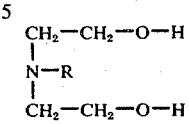

wherein R signifies an alkyl group containing from 12 to 18 carbon atoms. While the alkyl group may be a mixture of various fatty acids, one desirable source is tallow. A tallow tertiary amine having the above structural formula is supplied by the Armour Industrial Chemical Company, Chicago, Illinois under the tradename "Ethomeen T/12". The Ethomeen T/12 tallow fatty acid is sold as an antistatic agent for use on most hydrophobic fibers and is also known to have surfactant or wetting action properties.

Another source of an antistatic agent including a fatty acid tertiary amine is sold by Paint Products Laboratory of Chicago, Ill., under the trademane of "Statex PC-319". This product, comprising a fatty acid tertiary amine partially neutralized to the corresponding ammonium salt, as been used, for example, as an antistatic treatment for nylon, other textiles and airplane windows. While use of this material does reduce the surface resistivity to acceptable levels when applied to foam material, the treated foam does exhibit an undesirable lathering characteristic when vigorously rubbed with water present on the foam material.

It is a primary object of the present invention to provide a disposable surgical drape having an open-celled foam material on the outer surface in at least the primary operative area, wherein the foam material is treated to provide significantly improved desirable attributes.

More specifically, it is an object of the present invention to provide an improved surgical drape of the hereinbefore described type wherein the foam material is treated to equal or exceed surface resistivity values that are required for use in operating rooms or the like.

Still another object of the present invention provides for a surgical drape wherein the foam material is treated to produce the above mentioned surface resistivity and additionally exhibits superior rates of fluid absorbency.

Yet another object is to provide a surgical drape that exhibits the above desirable attributes, but which does not exhibit sudsing or lathering characteristics when rubbed with water present on the foam material.

A still further object of the invention lies in the provision of an improved surgical drape having all of the aforementioned desirable characteristics and yet which can be produced at such a low cost as to permit disposal of the drape after a single use.

A related object is to provide an improved surgical drape that enables the use of relatively low cost hydrophobic foam material, and yet results in superior rates of fluid absorption comparable to those exhibited by more expensive hydrophillic foam material.

Other objects and advantages of the invention will become readily apparent from the ensuing detailed description and accompanying drawings, in which.

Figure 1:
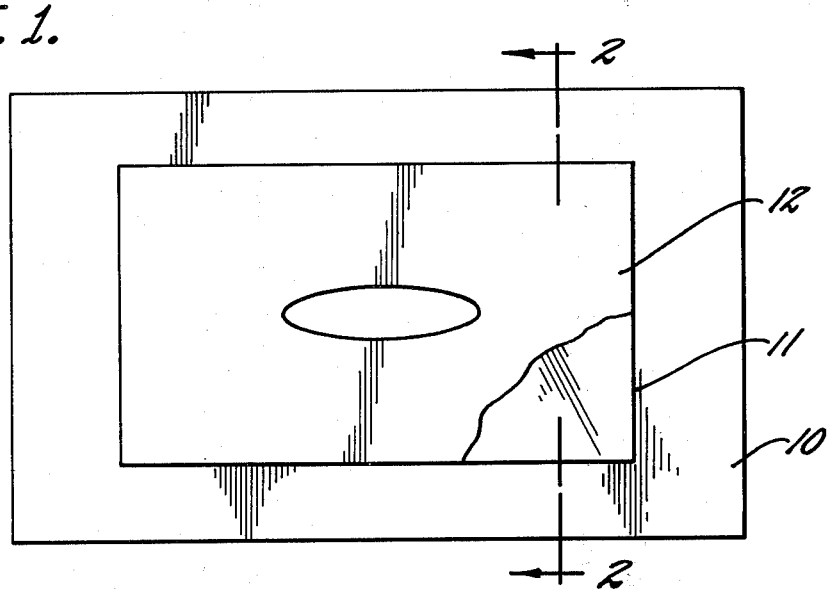
FIG. 1 is a plan view of a surgical drape embodying the present invention.
Figure 2:
FIG. 2 is a section taken generally along the line 2—2 in FIG. 1.

While the invention is susceptible of various modifications and alternative forms, certain specific embodiments thereof have been shown by way of example in the drawings and will be described in detail herein. It should be understood, however, that it is not intended to limit the invention to the particular forms disclosed, but on the contrary, the intention is to cover all modifications, equivalents and alternatives falling within the spirit and scope of the invention as expressed in the appended claims. In this connection, a laparotomy drape sheet has been shown in the drawings. It should be understood that other types of drape sheets may be used and that the invention is not limited to the type of drape sheet illustrated. Similarly, the specific embodiment of the base sheet is described as comprising outer layers of cellulosic wadding and inner layers of highly drafted fibers. It should be understood that the construction of the base sheet should not be limited to the specific base sheet disclosed.

Turning now to the drawings, there is shown a surgical drape having a primary operative area, which is the fenestration area of the illustrated laparotomy sheet. The drape has a fibrous base sheet 10, over which a fluid impervious plastic layer or film 11 is bonded. The film 11 may be bonded to the fibrous base sheet 10 by any suitable means, such as by means of an adhesive. The film 11 provides a fluid impervious barrier in the primary operative area so that any fluids contacting this area cannot strike through the sheet. This prevents the transfer of bacteria through the sheet and thereby helps insure that sterile conditions will be maintained in the primary operative area. It should be understood that the film must be capable of remaining stable under the conditions encountered in the particular treatment to which the drape sheet is subjected to render it sterile, e.g., temperatures of about 270°F for steam sterilization or about 160°F for sterilization by means of ethylene oxide or the like.

Examples of suitable films are polyethylene e.g., 2 mil. polyethylene film manufactured by Clopay Corp, Cincinnati, Ohio; polypropylene, e.g., "Extrel II" available from Extrudo Film Corp, New York, N.Y.; polyethylene methylacrylate co-polymer film manufactured by Edison Plastics Company; and vinyl chloride films. The film should be substantially free of pin holes to provide the desired sterility barrier, and thus must generally be at least 0.15 mil thick.

Overlying the fluid impervious film 11 is a foam material 12 which may be bonded to the film 11 by any suitable means, but preferably by means of an adhesive. The absorbency of the open-celled foam 12 prevents excessive fluid run-off and yet the absorbed fluids cannot strike through the drape because of the intermediate layer of fluid impervious film 11. The relatively high coefficient of friction of the foam material provides a substantially non-slip surface which prevents accidental dislodgement of surgical instruments and the like when they are placed on the surface of the foam material. In addition, the foam material 12 preferably has a low glare which is achieved in part by its open cellular structure and which may be enhanced by tinting or coloring the foam during its manufacture or subsequently. The foam thickness should generally be in the range of about 25 mils to about 100 mils, and the absorbency of the foam sheet should be at least about 150% by weight and for a 40-mil thick foam material preferably at least 575% and at least 4.5 gm/4-inch by 4-inch sample. Examples of suitable foams are 40-mil polyester polyurethane foam having a density of 1.7 lbs/ft$^3$, available from Reeves Brothers Inc., New York, N.Y. or Tenneco Chemicals Inc., New York, N.Y. and polyether polyurethane foams.

The base sheet 10 preferably comprises outer layers of cellulosic wadding and inner layers of highly drafted fibers disposed angularly relative to each other. A spaced pattern of adhesive is disposed between each fiber layer and its adjacent wadding layer with the fibers in each layer partially embedded in, and held by, the adhesive in the adjacent adhesive layer and partially embedded in, and held by, the adhesive in the outer adhesive layer where it extends between the fibers of its adjacent fiber layer and with a portion of the adhesive in both adhesive layers joined where the adhesive patterns are superimposed. This material is described in more detail in copending Sokolowski et al.

application Ser. No. 546,067, filed Apr. 28, 1966, now U.S. Pat. No. 3,484,330 and assigned to the assignee of the present invention.

Suitable adhesives for use in bonding the foam material to the film and for bonding the film the the base sheet are preferably water resistant adhesives that are solvent based, in solvents such as, for example, methyl ethyl ketone or ethyl acetate. One adhesive is a two component urethane solvent based system, available from the Chemical Division of Borden, Inc., Chicago, Ill. under the tradename "MA-5750". The adhesive is suitably applied to the film at a loading of about 2 to 10 grams per square yard and may be applied at room temperature. The adhesive is preferably applied in a spaced pattern to maintain flexibility. The pressure used to laminate the film to the foam material is relatively light, and is just sufficient to make good contact between the film and foam material. While the bonding of the film to the base sheet may be performed using similar adhesive and loading, the adhesive is preferably continuous around the fenestration and around the outer periphery of the film.

In accordance with the present invention, the foam material 12 is treated with an isopropanol-water solution of a fatty acid tertiary amine, partially neutralized to a carefully controlled level to the corresponding ammonium salt to achieve the necessary surface resistivity and superior rate of fluid absorbency and yet obviate the undesirable lathering property.

The treating solution thus includes the reaction product of a fatty acid tertiary amine having the structural formula:

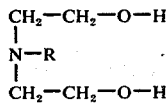

(wherein R signifies an alkyl group containing from 12 to 18 carbon atoms) and a mineral acid. Among the mineral acids that can be used are hydrochloric acid, sulfuric acid and phosphoric acid, although phosphoric acid is preferred. The alkyl group may consist of a single member or the amine may comprise a mixture having different alkyl groups. In the latter instance, it has been found desirable to use tallow as the source for R, viz.- the alkyl group.

In keeping with the present invention, the reaction product is preferably applied in an isopropanol water solution in sufficient quantity such that at least 0.125 gms/yd$^2$ add on is applied to the surface of the foam material. Although the solution may be sprayed upon the surface of the foam material, it has been found that flexographic printing of the solution is preferred, due to the fact that quantities are more easily controlled and there is less potential for creating a health hazard in terms of explosive vapor concentrations than may be present if the solution is sprayed upon the surface of the foam material. The particular solvent in which the compound is dissolved has been found to be important. It is preferred to use an isopropanol-water solvent wherein the isopropanol comprises between about 30 and 80% by weight of the solvent. If less than about 30% isopropanol is used, it has been found difficult to dissolve the compound. If more than 80% isopropanol is used, the antistatic properties of the resulting drape may be decreased below acceptable limits as set forth in the hereinbefore mentioned Code.

Since the fatty acid tertiary amine is known to be a wetting agent of surfactant, it would be expected that the free amine is the cause of the lathering or sudsing characteristic. It would accordingly be assumed that the lathering characteristic would be minimized by tying up or neutralizing the free amine. Thus, it would be anticipated that the greater the extent of neutralization (causing a concomitant reduction in the pH), the less lathering or sudsing would be a problem. Contrary to expected belief, however, it has been found that neutralization must only be carried out to a certain level, because further neutralization in fact results in the unwanted lathering property in the treated drape.

To achieve the objectives of the present invention, the amounts of mineral acid and amine should thus be controlled to provide neutralization of the amine to an extent not greater than about 34%. In keeping with the present invention the degree of neutralization can be obtained by maintaining the pH within carefully controlled limits. To this end, by insuring that the pH does not drop below about 7.5 (as measured by a pH meter having water in the probes) desired neutralization will result.

Where phosphoric acid is used and the pH of the treatment is about 7.5 or greater, it is believed that the principal reaction product has the following structural formula

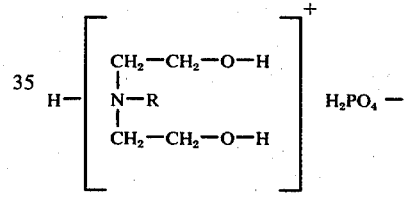

wherein R signifies an alkyl group containing from 12 to 18 carbon atoms.

In accordance with a further aspect of the present invention, it has been found that if the solution has a pH of greater than about 8.5, it is more difficult to dissolve the reaction product in the solvent unless the solvent contains a greater amount of isopropanol and, additionally, the reaction product tends to precipitate out. As previously mentioned, the antistatic properties of the foam may be impaired if the percentage of isopropanol in the solvent exceeds about 80%.

In keeping with the present invention, it has been found that the treatment of the foam material with the above mentioned reaction product also significantly improves the rate of absorption of liquids that come in contact with the foam material. While an open-celled foam material, even if it is normally hydrophobic, will absorb fluids, normally hydrophobic open-celled foam material often requires considerable time before the fluid is absorbed into the cellular structure of the foam material. It should be understood that the rate of absorbency of the foam material is important since any liquids that come in contact with the foam material during an operation should preferably be readily absorbed rather than remain on the foam material surface where a physician or other member of a surgical team would contact the fluid. Although polyurethane foam having some degree of hydrophilicity is commercially available, the cost of such foam is substantially greater than commercially available hydrophobic polyurethane foam material. The present invention, in addition to providing surface resistivity values within the prescribed range as required by the Code, has the additional effect of providing greatly increased rates of fluid absorption, all of which may be achieved at a much lower cost since normally hydrophobic foam material may be used.

As one specific example of treating the foam material in accordance with the present invention, a disposable surgical drape having exposed 40-mil polyester polyurethane, open-celled foam material was treated with a isopropanol water solution of the reaction product of the tallow fatty acid tertiary amine and phosphoric acid with the solution being adjusted to have a pH of about 7.5. The isopropanol-water solvent contained about 40% isopropanol and approximately 6.2% solids of the tallow fatty acid tertiary amine that was about 34% neutralized to the tallow fatty acid ammonium salt with phosphoric acid. The solution was printed upon the outer surface of the foam material such that about 0.125 gm/yd$^2$ add-on of the reaction product was present after drying to eliminate the solvent. It was found that the rate of water absorbency as measured by placing drops of water on the surface and measuring the time required for it to be absorbed into the foam material was less than a few seconds the majority of the time as compared to in excess of 300 seconds for untreated hydrophobic polyurethane foam. Similar tests were run to measure the rate of absorption for drops of 1% sodium chloride solution which is generally known as saline solution often used in surgical operations. Drops of the saline solution were generally absorbed in about 1 to 7 seconds as compared to in excess of 300 seconds for untreated polyurethane foam material. Surface resistivity values of the treated foam material measured in accordance with AATCC test method 76–1969 were about $1 \times 10^{10}$ ohms per square unit as compared to about $5 \times 10^{12}$ ohms for nontreated foam. The foam material did not exhibit foaming when it was vigorously rubbed in the presence of water.

Thus, the disposable surgical drape of the present invention has been shown to exhibit superior rates of absorption characteristics as well as satisfy the surface resistivity requirements of the National Fire Protection Association and failed to exhibit the unwanted lathering characteristics.

What is claimed is:

1. A method for treating a normally hydrophobic, open-celled polyurethane foam for use on the surface of a disposable surgical drape or the like, to reduce the surface resistivity of the foam to less than $5 \times 10^{11}$ ohms, increase the rate of fluid absorption thereof and minimize the tendency of the treated foam to lather when rubbed in the presence of water, comprising the steps of:

applying to the surface of the foam an isopropanol-water solution of the reaction product of a mineral acid and a fatty acid tertiary amine, said fatty acid tertiary amine being neutralized less than about 34% to form a fatty acid tertiary ammonium salt, said fatty acid tertiary amine having the structural formula:

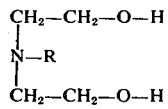

wherein R signifies an alkyl group containing from 12 to 18 carbon atoms; said solution being applied in sufficient quantity to apply at least about 0.125 gms/yd$^2$ of said reaction product to the surface of said foam.

2. A method as defined in claim 1 wherein the pH of said solution is preferably at or above about 7.5.

3. A method as defined in claim 1 wherein said solution is printed on the surface of said foam.

4. A method as defined in claim 1 wherein said solution contains approximately 6.2% solids of said reaction product in said isopropanol-water solvent wherein isopropanol comprises about 30 to about 80% by weight of said solvent.

5. A method as defined in claim 1 wherein said mineral acid is selected from the group consisting of phosphoric acid, sulphuric acid and hydrochloric acid.

* * * * *